United States Patent [19]
Zimmermann et al.

[11] 4,220,916
[45] Sep. 2, 1980

[54] METHOD OF AND APPARATUS FOR DETERMINING THE BREAKDOWN CHARACTERISTICS AND SIZE OF MEMBRANE-SHEATHED PARTICLES SUCH AS CELLS

[75] Inventors: Ulrich Zimmermann, Jülich; Günter Pilwat, Niederzier; Michael Groves, Jülich, all of Fed. Rep. of Germany

[73] Assignee: Kernforschungsanlage Jülich Gesellschaft mit beschränkerter Haftung, Jülich, Fed. Rep. of Germany

[21] Appl. No.: 29,842

[22] Filed: Apr. 13, 1979

[30] Foreign Application Priority Data

Jun. 28, 1978 [DE] Fed. Rep. of Germany ....... 2828232

[51] Int. Cl.² .......................................... G01N 27/07
[52] U.S. Cl. ................................. 324/71 R; 324/446
[58] Field of Search ................ 324/71 R, 71 CP, 442, 324/446

[56] References Cited

U.S. PATENT DOCUMENTS

| | | | |
|---|---|---|---|
| 4,055,799 | 10/1977 | Coster et al. | 324/71 R |
| 4,168,460 | 9/1979 | Menke | 324/71 CP |

*Primary Examiner*—Alfred E. Smith
*Assistant Examiner*—Charles F. Roberts
*Attorney, Agent, or Firm*—Karl F. Ross

[57] ABSTRACT

A method of and an apparatus for determining the dielectric breakdown characteristics and size of membrane-sheathed particles such as living-organism cells and the apparent size of such particles after breakdown of the membrane, makes use of two measuring orifices traversed by an electrolyte across which an increasing electric field is applied during the measuring process in which the particles successively traverse one of the orifices. The current through the measuring orifice deviates from the linear with increasing field generated preferably by a sawtooth voltage, the current change being used to measure the particle variables stated.

10 Claims, 4 Drawing Figures

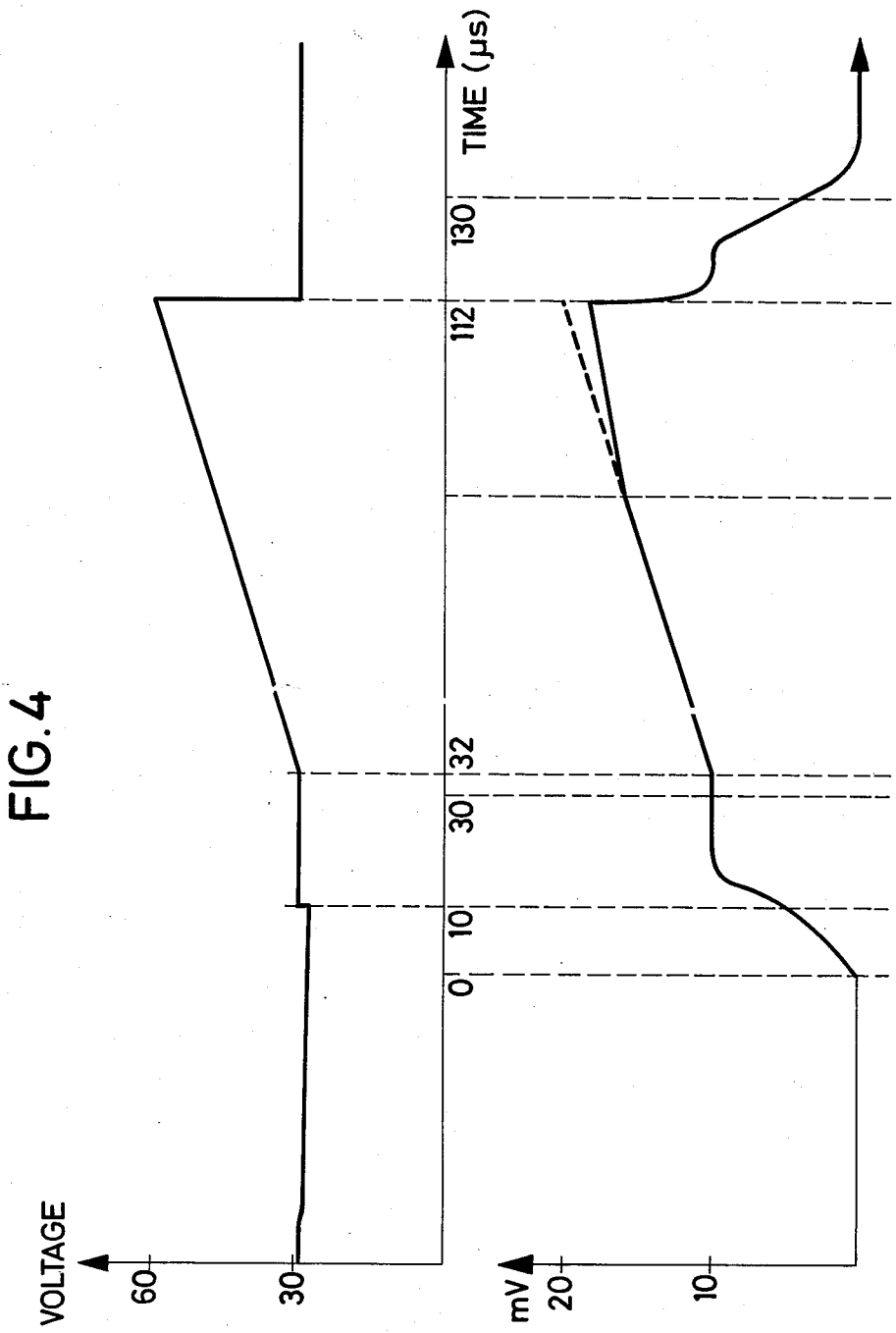

METHOD OF AND APPARATUS FOR DETERMINING THE BREAKDOWN CHARACTERISTICS AND SIZE OF MEMBRANE-SHEATHED PARTICLES SUCH AS CELLS

FIELD OF THE INVENTION

The present invention relates to a method of and to an apparatus for determining the dielectric characteristics and size of particles enclosed in a membrane susceptible to dielectric breakdown, and the virtual size of such particles subsequent to breakdown. More particularly, the invention relates to improvements over the systems described in our U.S. Pat. No. 4,055,799 and German Pat. No. 2,502,621.

BACKGROUND OF THE INVENTION

The aforedescribed patent describes a process and an apparatus for determining the dielectric breakdown characteristics of electrolyte-suspended particles having membranes, especially organic cells derived from living organisms, especially liposomes, protoplasts, chloroplasts, vacuole cells or the like and for determining the size of the particles and other characteristics thereof subsequent to dielectric breakdown.

In the earlier process, the particles, usually biological cells, were suspended in a physiological liquid which served as an electrolyte solution which traversed a measuring opening or orifice. In this system, the particles lodge and are immobilized in the opening, on both sides of which electrodes are provided. The electrodes are energized by a voltage which is increased until dielectric breakdown occurs and the change in the current passing between these electrodes is measured.

The particles which are thus subject to dielectric breakdown must then be removed from the measuring opening, e.g. by suction, so that new particles can be fixed or lodged therein to enable a subsequent measurement.

A determination of the size or volume of the particles is not possible by this technique although it is known to determine the size of such particles from the increase in the electrical resistance which results in the current path through the measuring opening by the presence of the particle immobilized at the latter.

The processes of the aforementioned patents can be used for a variety of purposes. For example, it can be used to determine the characteristics of the particles or their membranes or cells so as to detect the influence of foreign agents thereon or of the cells upon other biological systems. For example, the effect of pharmaceutical agents or poisons or other materials on the cells of living organisms, in any concentration, can be evaluated by this system. In addition, the system can be used for investigations into the effect of diseases and biological conditions upon the cells.

The system provides information as to the condition and structure of the membranes or the size of the particles, the information being useful clinically to detect pathological cells or cell changes which manifest pathological conditions. The technique has also been found useful in determining the effect of chemotherapy or pharmaceutical therapy upon erythrocytes and tissue cells.

While the earlier process has been found to be highly effective for the purposes described, it has been determined that improvement is possible, especially with respect to the precise determination of the aforedescribed variables (dielectric breakdown of the membranes, particle size prior to breakdown and virtual size of the particles after breakdown) in that the static measuring methods are not sufficiently rapid when a large number of measurements must be taken and numerous particle variables extended, and a wide range of particle sizes may be involved.

The reason for this is that the measurements taken by the prior system were predominantly static in nature. The particles individually had to lodge in the measurement opening or at the mouth thereof and then had to be removed before a further measurement could be taken.

Furthermore, since the effect of different particles on the electric field because of the partial blockage or complete blockage of the measuring opening, varied with different particle types and size and particle size distributions, time consuming standardization operations were inevitable to provide useful information.

Thus the system, while successful as far as it went, could not provide rapid and fully reproducible measurements for a variety of cell types using only small numbers of cells. This was especially disadvantageous when the technique also used the presence or existence of pathological cells by high speed testing. Statistically significant results frequently could not be obtained.

OBJECTS OF THE INVENTION

It is the principal object of the present invention to provide an improved process for, or method of, determining the dielectric breakdown and size of membrane-sheathed particles of the class described and the apparent size of such particles upon dielectric breakdown.

Another object of this invention is to provide an improved method of ascertaining the dielectric property of cells from living organisms of the character described whereby the disadvantages of the earlier system are avoided.

Another object of the invention is to provide an improved method of the character described in which it is no loger neccessary to evaluate particles which have lodged in a measuring opening prior to subsequent measuring step and which can carry out the measurements reproducibly, rapidly and accurately with a minimum number of particles or cells and in spite of the availability of cells of a wide range of volumes or particle sizes.

It is also an object of the invention to provide a method of determining the nature of membrane-sheathed particles, such as living-organism cells, which will enable a rapid determination to be made for a large number of particles in succession and will afford a significant evaluation of the cell type.

Still another object of the invention is to provide a method which improves upon and extends some of the principles originally set forth in the above-identified patents.

A further object of our invention is to provide an apparatus for carrying out the improved method or process of the present invention.

SUMMARY OF THE INVENTION

These objects and others which will become apparent hereinafter are attained in accordance with the present invention, by passing the particles continuously through a measuring opening and each time, while they traverse the opening and are in movement therethrough, subjecting the particles to a linearly increasing electric field (rising, say, to 100 volts) and, from the speed of the particles with respect to the length of the measuring opening or orifice, the electric field and the change in the current through the orifice, determining the dielectric breakdown of the particles, the field strength being sufficient to effect such breakdown. The increase in the current traversing the measuring opening, while a particle is passing therethrough, deviates from linearity and the resulting change in current, by comparison with the linear increase in current through a reference passage not traversed by the particles is an indication of the size of the particle prior to dielectric breakdown and the apparent size of the particle subsequent to dielectric breakdown.

The process of the present invention thus permits, in a single measuring step for a given particle within the measuring opening, all of the data to be obtained for the three particle variables or parameters which are required. The data is preferably introduced into an arithmetic, calculator or computer unit simultaneously with the measuring step so that this unit can compare the data with previously stored data representing particle characteristics and afford an immediate indication of particle size prior to breakdown, apparent particle size subsequent to breakdown, and the dielectric breakdown voltage of the membrane, as well as an indication of the nature of the particle if so desired.

The determinations of the size of the particles prior to dielectric breakdown and the apparent size of the particles subsequent to breakdown, the size of the cells and the nature of intercellular fluids can be determined.

In a particular advantageous embodiment of the method aspect of the present invention and in the preferred mode of carrying out the invention in practice, a constant electric field is applied across the measuring opening to be traversed by the particle and as a particle enters the measuring opening, the resulting current change is used to determine the size of the particle prior to dielectric breakdown and to trigger the linear increase in the voltage to effect a dielectric breakdown. During the linear voltage increase the current change is used to make a second estimate of the size before breakdown, the breakdown voltage and the apparent size after breakdown. Thereafter, the voltage can be returned to a constant-voltage mode to prepare the measuring opening for receipt of the next particle.

This preliminary determination of the sizes of the particles prior to applying to the orifices the linear increase in the voltage can be used to provide a preselection of the particles. In this case, for a variety of particles traversing the measuring opening, dielectric breakdown determinations need be made only for those particles whose preliminary determined sizes makes evaluation necessary or desirable. The remaining particles can be simply passed without such determinations.

Using conventional high-speed electronic calculators or computer circuitry it has been found that extremely high measurement speeds can be utilized so that each measurement can be effected in a small fraction of a second. In practice, the speed of the particles through the measuring opening should be such that the residence time of a particle within the passage is about 20 to 200 microseconds. Such measure intervals have been found to be far less than can be obtained with prior apparatus or process for measuring dielectric breakdown etc.

An important advantage of the system of the present invention, related to the high speed with which each measurement can be taken and hence the large number of measurements which can be taken with relatively short time, is that statistically significant results for a large population of cells can be obtained. It is for this reason that rapid evaluation of the data in combination with rapid determination of the data is important.

In order to carry out the invention in practice, we have found that the apparatus for performing the method or process should have, in addition to the measurement opening or passage mentioned previously and the electrodes in chambers upstream and downstream of the passage for applying the constant and linear voltage, a second or reference measuring opening or passage which is traversed by a branched particle free electrolyte stream identical to the electrolyte stream traversing the measuring passage and across which a corresponding electric field is provided.

The electrodes, in this case, are so arranged that the same field strengths are applied across the two measuring passages and are subject to linear increase with an increase in the applied voltage.

According to a feature of the invention, the electrodes on the outlets of the two passages are connected to a current/voltage converter which transforms the amplitude of the current traversing the respective passage into a corresponding voltage.

Means are then provided in connection with this converter to form a difference signal from the two voltages, the difference signal being processed to yield the data mentioned previously.

The circuitry of the present invention also preferably includes means responsive to the entry of a membrane-sheathed particle into the measuring passage for initiating a linear increase in the electric field strength and the voltage over a predetermined measuring interval and thereafter returning the voltage to its original value.

The use of a reference passage, electrode system, current/voltage converter, etc., for the simultaneous generation, during the measurement interval, of a reference signal has been found to be especially effective in eliminating transients or errors which may result from modifications of the electrolyte supply or feed, temperature and the like. Naturally, if desired, measurements can be made in either chamber or passage.

The two openings or passages should have the same dimensions which we have found should include a length of 50 to 500 microns and a diameter of 20 to 200 microns, naturally depending upon the nature of the particles to be examiner. The passages should have circular cross sections.

According to a feature of the invention, circuit means is provided to respond to the entry of a particle into one of the measuring passages and for maintaining a constant voltage across these openings for a predetermined interval (in which the size of a particle is measured), and only after the lapse of this interval is the linear increase of the voltage triggered. In this embodiment of the invention it is possible to provide that only those particles of an interesting particle size will be found analyzed.

According to another embodiment of the invention, a unit is provided for superimposing on the voltage applied across the electrodes during the constant/voltage mode, an alternating current signal of a frequency of 1 to 10 kHz, this unit being connected as well to the differential amplifier or, more particularly, the means for generating the difference signals by means of a phase-lock amplifier. This circuit is designed to ensure that during this application of this alternating current, no difference signals are outputted to, for example, the analog/digital converter. As a result, the system is held in an automatic zero or null condition in the absence of a particle and the device will not respond to temperature fluctuations and the like perturbations which may arise in the vessel, electrolyte etc. Thus the temperature drift can be held to an effective level below 0.005° C. and relative resistance changes because of system noise and disturbances can be held, in terms of relative resistance difference between the two measuring openings to not more than 0.0001.

BRIEF DESCRIPTION OF THE DRAWING

The above and other objects, features and advantages of the present invention will become more readily apparent from the following description, reference being made to the accompanying drawing in which:

FIG. 4 is a waveform diagram illustrating voltage vs. time characteristics of the measurement made with the system of the present invention.

SPECIFIC DESCRIPTION

Figure 1:
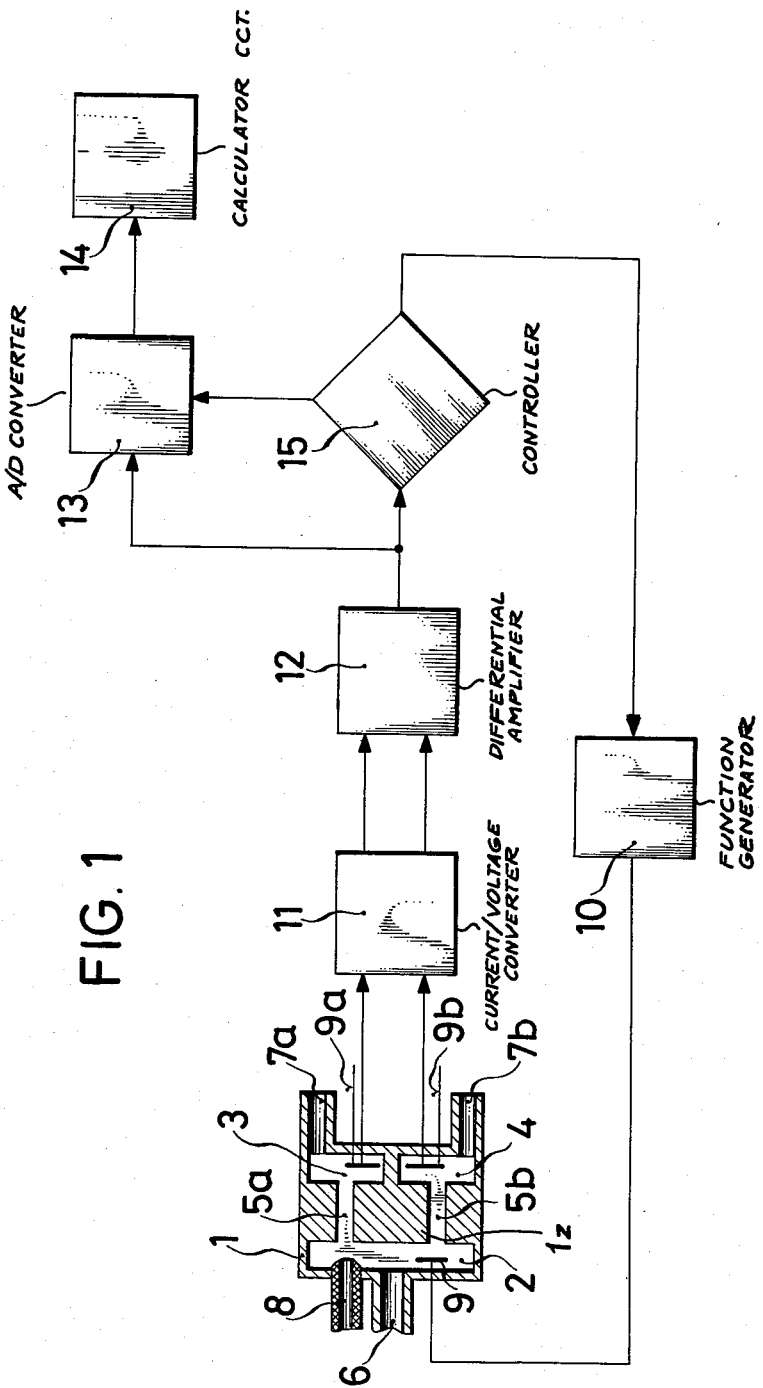
FIG. 1 is a diagrammatic illustration of an apparatus for carrying out the method of the present invention, showing the measuring unit in axial cross section and the circuit in block-diagram form.

In the diagram of FIG. 1, the vessel 1 is subdivided into three chambers 2, 3 and 4. The partition 1z subdivides the interior of the vessel 1 into the chamber 2 on one side and into the chambers 3 and 4 on the opposite side. The partition is formed with a pair of measuring openings or orifices 5a and 5b which are identical in diameter and length and are so positioned as to, respectively, connect the chamber 3 and the chamber 4 with chamber 2.

Chamber 2 is provided with an inlet fitting 6 for the supply of electrolyte solution to the chamber 2 while the chambers 3 and 4 each have an outlet fitting 7a and 7b, respectively, from which the electrolyte is discharged.

A further inlet fitting 8 opens into the chamber 2 to deliver the particle-containing suspension, this fitting having its outflow trained upon the orifice 5 and being axially aligned therewith.

This ensures that the particles will be directed centrally into the measuring orifice 5a and will traverse the latter along with the electrolyte passing simultaneously through this orifice and the reference orifice 5b.

By means not shown (e.g. a variable-displacement pump or valve upstream of the inlet fitting 6 or a pump downstream of the outlet fittings 7a, 7b) the flow of electrolyte can be introduced under pressure into the chamber 2 or withdrawn from the chambers 3 and 4 to ensure a fluid pressure gradient across the orifice 5a, 5b from the left-hand side of the vessel to the right-hand side thereof.

Electrodes 9, 9a and 9b extend into the respective chambers 2, 3 and 4 (see U.S. Pat. No. 4,055,799 and German Pat. No. 2,502,621).

As can be seen from FIG. 1, moreover, the electrodes 9, 9a and 9b are connected with electric circuitry to apply the linearly increasing voltage and measure the current changes in the manner described. More particularly, the electrodes 9 are connected, as has only been schematically represented, by the block diagram of FIG. 1, to a function generator 10 capable of producing a constant voltage (constant-voltage mode) and a sawtooth voltage (sawtooth mode) which can be applied across the orifices 5a and 5b and hence across the flow cross section traversed by a particle within the orifice 5a, this voltage creating a corresponding voltage gradient across the orifice and establishing a voltage field of a predetermined field strength thereacross.

The electrodes 9a and 9b are also connected to a converter circuit 11 comprising two current-voltage converters (see FIG. 3) whose output voltage signals are applied to a differential amplifier 12 which subtracts the voltage signal associated with orifice 5b from the voltage signal associated with orifice 5a.

The resulting difference signal is then applied to an analog-digital converter 13 which delivers its output pulses to an arithmetic or calculator unit (computer) 14.

Upon entry of a particle into the measuring orifice 5a, a change in the resistance within the orifice to the current traversing same is detected at the corresponding input to the current-voltage converter 11 and is manifested in a voltage change at the corresponding input to the differential amplifier 12.

The differential signal thus produced is applied not only to the A/D converter 13 but also to a controller 15 which, after a predetermined delay time, triggers the function generator 10 into its sawtooth mode if the signal was of appropriate size and, after the lapse of another interval of predetermined duration, allows the function generator 10 to revert to its constant-voltage mode.

During the sawtooth-mode operation of the function generator 10, the A/D converter 13 is turned on by the controller 15. Upon the lapse of the measuring interval (between ON and OFF states of the A/D converter 13 and during the sawtooth-mode operation of the function generator 10) a measurement is made. Upon the lapse of this interval, the system is ready to carry out the measurement for another particle traversing the orifice 5a.

Figure 2:
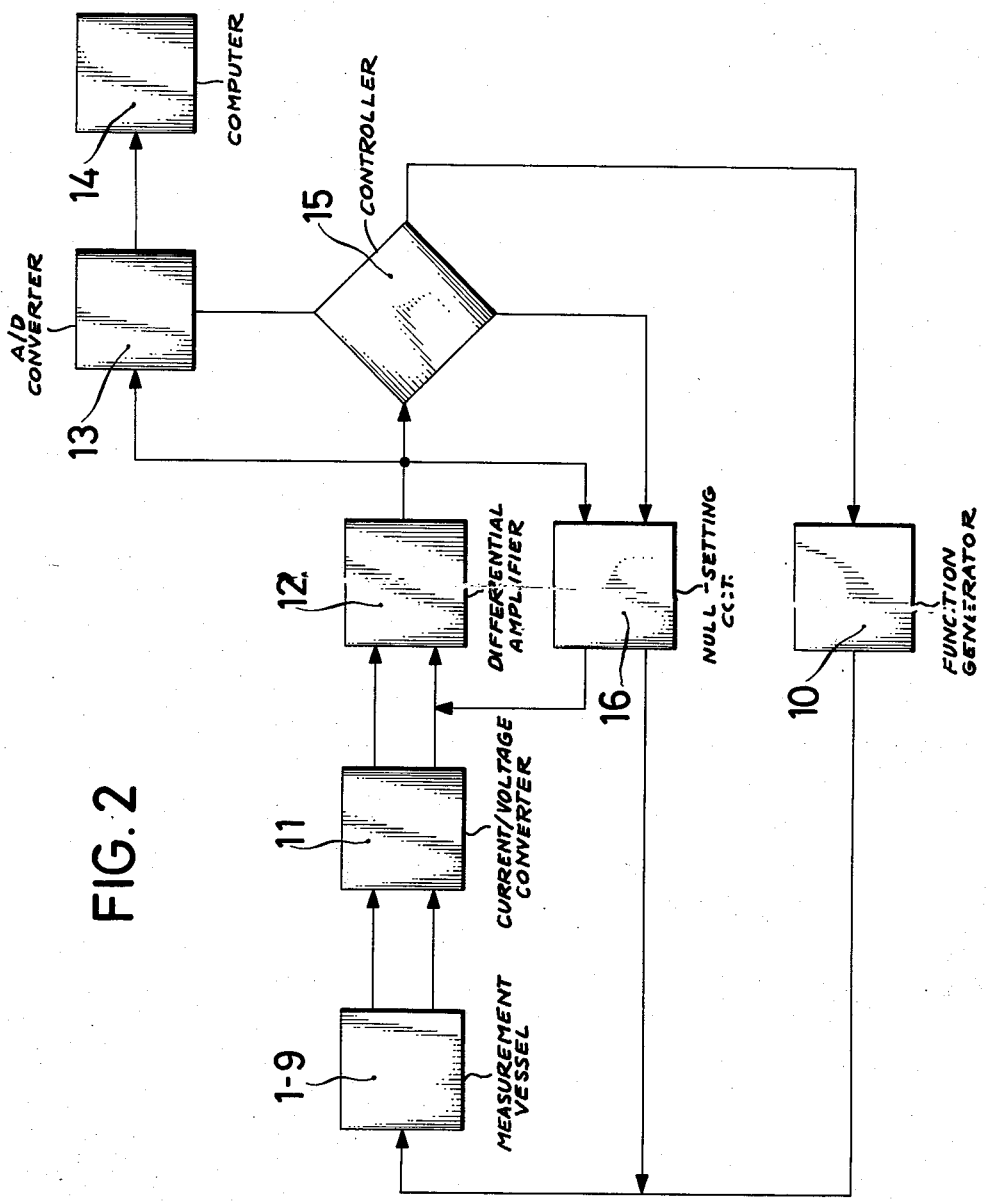
FIG. 2 is a block diagram of a system similar to that of FIG. 1, but additionally provided with a zeroing circuit.

FIG. 2 shows another system, also in block diagram form, for effecting measurements as described. In this system the measurement vessel and associated parts have been illustrated as the block 1–9 and of course are identical to those described with reference to FIG. 1.

Other elements according to those of FIG. 1 have been given the same reference numerals as previously used therein.

Thus, the electrodes of the measurement vessel 1–9 are applied to the current voltage converter 11 which outputs to the differential amplifier 12. The different signal is here also applied to the controller 15 and to the A/D converter 13 which feeds the computer 14. The controller triggers the A/D converter 13 and the function generator 10 in the manner described.

In this embodiment, however, a zero-setting unit 16 is provided for the NULL-setting of the difference signal. The zero-setting unit 16 includes a high-frequency alternating-current generator 16d which is triggered by the controller 15 during the interval in which no particle traverses the measuring passage 5a so as to superimpose upon the constant voltage of the function generator 10 a high-frequency alternating current of, for example, 3 kHz. The differential amplifier 12 is so set that the alternating signals are compared and no difference signal is outputted upon detection of this alternating voltage.

As soon as a particle enters the orifice 5a, however, the change in current flow at this orifice is detected as noted previously and causes the controller 15 to cut off the AC generator 16a and terminate the automatic zero-pointing setting.

Figure 3:
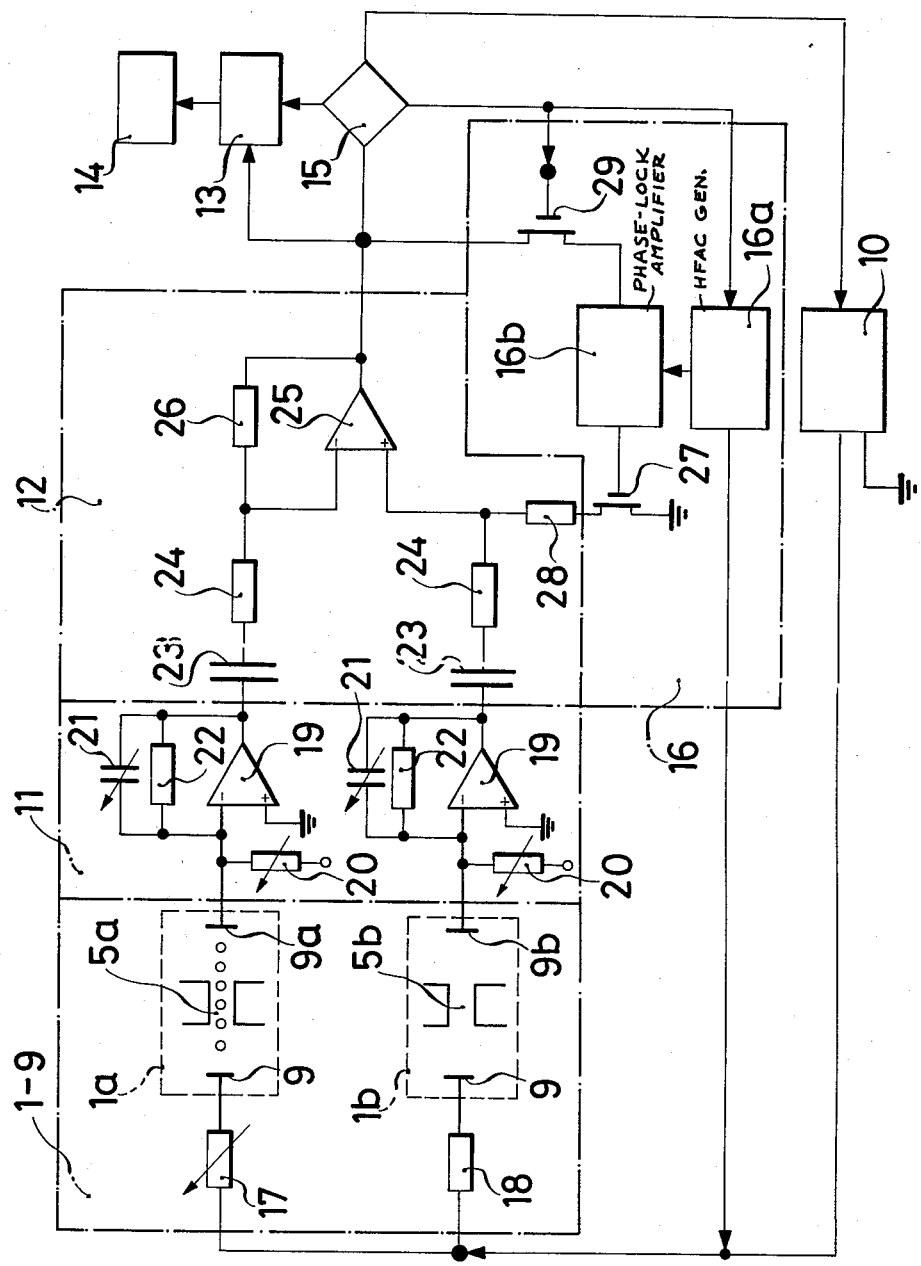
FIG. 3 is a circuit diagram illustrating electronic components of some of the units of the systems of FIGS. 1 and 2 in greater detail.

FIG. 3 shows the circuit elements of FIGS. 1 and 2 in greater detail. The vessel of FIGS. 1 and 2 is here represented and is constituting the flow cells 1a, 1b which are both traversed by electrolyte and include the identical orifices or passages 5a and 5b, described fully earlier. Cell 1a is the measurement cell and 1b is the reference cell.

One output of the function generator 10 is grounded or connected to a common busbar as represented by the normal ground symbol. The function generator output is applied through level setting resistors 17 and 18, at least one of which is adjustable to enable the system to be balanced with a flow of electrolyte before particles are introduced. In the embodiment shown, the resistor 18 is a fixed resistance with a value of, say, 2.5 k$\Omega$ while resistor 17 is a potentiometer with a value controllable up to 5$\Omega$.

The current/voltage converter 11 comprises two operational amplifiers 19 (INTERSIL 2525) whose output terminals are connected to a voltage of opposite polarity to the function generator voltage for direct-current compensation using balancing potentiometers 20 adjustable to values of up to 5$\Omega$ each. The operational amplifiers 19 are bridged by high-frequency-trimmer condensers 21 of capacitance values of 60 pF each. Feedback resistors 22, each of a value of 35 k$\Omega$, also bridge these operational amplifiers 19.

In the connections between the converter 11 and the differential amplifier 12 forming the difference signals, there are provided AC coupling capacitors 23, each having a capacitance value of 1 $\mu$F as well as resistors 24 of 11 k$\Omega$ each. The difference circuit uses a differential amplifier 25 of the INTERSIL operational amplifier 2525 type with feedback through 110 k$\Omega$ resistor 26.

The null-setting circuit 16 comprises a phase-lock amplifier 16b and a high-frequency alternating current generator 16a. The phase-lock amplifier 16b outputs via a CMOS-FET 27 in series with 110 k$\Omega$ resistor 28 to one of the inputs of the differential amplifier 25 and is connected to the output thereof via an FET switch 29 (MC 140 16 CP) which is triggered by the controller 15.

In this circuit arrangement the alternating voltage from the generator 16a is fed across the measuring orifices 5a and 5b, whereby any deviation from equality of these orifices, results in a voltage different from zero which is phase dependent at the differential amplifier 25. This difference signal, detected at the phase-lock amplifier 16b, results in integration of the phase-dependent alternating voltage until the voltage level at the gate formed by FET 27 is substantially great to develop equal-magnitude input signals at the differential amplifier 25 and a zero output.

The integrated output signal of the phae-lock amplifier 16b is thus used to compensate deviations from zero by change in the amplification of the non-inverting part of the differential amplifier 25 with the aid of the FET 27 which is used as an electrically adjustable resistor. As soon as a particle enters the measuring passage 5a, however, and the resistance change triggers the controller 15, the alternating-current generator 16a and the phase comparison circuit are cut off.

FIG. 4 shows at its upper part the applied voltage (ordinate) vs. time in $\mu$sec (abscissa), while the lower diagram shows the corresponding difference signal at the differential amplifier 12.

By comparing these two curves, it will be seen that a constant voltage with a small superimposed sine wave is applied up to the time 0 which corresponds to the beginning of a measurement, namely, the entry of the particle into the measuring passage 5a. Prior thereto, the difference signal is of course null.

Upon entry of a particle into the measuring opening, the resulting resistance change causes a change in the current through the measuring passage and hence a rise in the difference signal. The controller 15 cuts off the alternating voltage supplied by the generator 16a while maintaining the constant voltage from the function generator.

During this phase of the measurement, the size of the particle is determined by pulse-height analysis, and, from the size, the computer can determine whether or not further analysis is desired or whether the particle simply should be passed.

At a predetermined interval, in this case 32 $\mu$sec after the presence of the particle in the passage was detected, the function generator 10 applies a linear voltage increase in the form of a sawtooth which rises during the time interval between 32 and 112 $\mu$sec.

At the end of this measuring interval, the voltage is dropped to its original value and the particle leaves the measuring orifice so that at about 130 $\mu$sec after the start of the measurement the difference signal has returned to its original value and the null-setting unit 16, with the alternating-current generator 16a, is again turned on. Breakdown of the membrane is detected in the form if a sudden drop in the rate of change of the difference voltage within the interval between 32 and 112 $\mu$sec and apparent particle size after breakdown can be measured by the slope of the difference signal after breakdown.

SPECIFIC EXAMPLE

In the embodiment of FIGS. 2 and 3, in which the measureing and reference passages each have a diameter of 70 microns and a length of 150 microns, the particle parameters of erythrocytes obtained from 1.6 ml of human blood and containing 0.4 ml of 3.8% trisodium-citrate 5.5 hydrate as anticoagulant were ascertained.

20 $\mu$l of the aforedescribed solution were metered into 10 ml of an isotonic phosphate-buffered solution (aqueous) containing 130 mmol/l of sodium chloride, 12.3 mmol/l of disodium hydrogen phosphate and 2.7 mmol/l of monosodium dihydrogen phosphate. The solution had a conductivity of 0.0158 mhO/cm.

The size determination was based upon a standardization with latex particles of known diameter.

$10^5$ measurement procedures were carried out with the particle size of the erythrocytes being determined during the application of the linear voltage increase by the rise of the difference signals prior to dielectric breakdown. From this particle size distribution, based upon a form factor of f=1.09, the mean volume of the erythrocytes was determined to be 85.1 microns$^3$. From the ratio of the increase in the difference signals prior to and subsequent to dielectric breakdown the conversion factor for the mean apparent value was found to be 0.613 and the apparent volume subsequent to breakdown was determined as 52.2 microns$^3$.

The critical potential difference at which the particle underwent dielectric breakdown was determined at the intersection or inflection point of the two slopes of the difference signals which correspond to the critical field strength in the measuring passage. From the integrated La Place equation and the form factor of the erythrocytes, the potential $V_{mc}$ at this point was determined by the relationship:

$$V_{mc} = f \cdot a \cdot E$$

where E is the critical field strength, a the large half axis and f the form factor. For the mean volume of the erythrocytes (85.1 microns$^3$), f=1.09, a=6.6 microns and E=1112 volts/cm, $V_{mc}$=0.8 volts.

The apparent volume subsequent to breakdown of the erythtocytes can provide other calculable values of interest, such as the quantity of hemoglobin per cell. This is because the erythrocyte cells consist, aside from the membrane, essentially of hemoglobin. To enable this calculation, the requisite conversion factors were obtained from 40 different blood tests of the hemoglobin content of erythrocytes photometrically by the hemoglobin-cyanite method and correlated with the apparent volume after breakdown. The conversion factor was 0.179 pg hemoglobin/microns$^3$. Thus, the hemoglobin content per cell was calculated using the apparent volume of 52.2 microns$^3$ to be 37.5 pg.

The number of cells in the afore-mentioned suspension which traversed the measuring passage was 34,437 in 5.33 μl of the suspension, considering the dilution factor of 625.25 which yielded 4.0 Mio cells/μl. The hemoglobin concentration is calculated to be 15.2 g/100 ml, using the value 37.5 pg hemoglobin per erythrocyte.

It was further found that after dielectric breakdown of the membrane of erythrocyte ghost cells which were already subjected to dielectric breakdown and contained the same conductivity solution inside the cell as that used in the measurement, cause the difference signal to be substantially parallel to the time axis (FIG. 4) which suggests the utility of the method of the invention and the apparatus in measuring the intracellular conductivity of such particles.

We claim:

1. A method of determining the size and dielectric breakdown characteristics of a membrane-sheathed particle and the apparent size thereof after dielectric breakdown which comprises the steps of:
   (a) entraining the particles through a measuring passage in an electrolyte solution;
   (b) applying across said measuring passage a linearly increasing electric field causing the passage of an electric current through the electrolyte traversing said passage;
   (c) detecting the breakdown characteristics of the membrane of the particle upon the increase in the strength of said field;
   (d) automatically detecting the change in electric current traversing said passage as a result of the presence of said particle prior to dielectric breakdown of said membrane, thereby ascertaining the size of the particle prior to dielectric breakdown; and
   (e) automatically detecting the effect of the particle on said current subsequent to dielectric breakdown to measure the apparent size of the particle subsequent to breakdown of said membrane.

2. The method defined in claim 1 wherein, in traversing the passage, the particle is subjected first to a constant electric field prior to the application of the linearly increasing electric field, the determination of the size of the particle prior to dielectric breakdown of said membrane in step (b) being effected during the application of said constant electric field.

3. The method defined in claim 1 wherein the particle is entrained through said passage in the electrolyte solution with a speed such that the residence time of the particle in said passage is from about 20 to about 200 microseconds.

4. An apparatus for determining size and dielectric breakdown characteristics of membrane-sheathed particles, said apparatus comprising:
   a measuring vessel formed with an inlet compartment and a pair of outlet compartments each communicating with the inlet compartment through a respective passage, one of said passages constituting a measuring passage and the other of said passages a reference passage, means for introducing an electrolyte solution into said inlet compartment whereby said electrolyte traverses said passages into said outlet compartments, means for discharging electrolyte from said outlet compartments, and electrodes in said compartments, said inlet compartment being further provided with a particle inlet aligned with said measuring passage whereby membrane-sheathed particles are induced to traverse said measuring passage;
   a function generator connected to said electrodes for simultaneously applying across said passages indentical electric fields of linearly increasing field strength so as to pass respective electric currents through said passages, the current flow through said measuring passages being modified upon the traversal of said measuring passage by a particle entrained by said electrolyte;
   a current/voltage converter connected to the electrodes of said outlet compartments for transforming the currents traversing said passages into respective voltages;
   comparator means connected to said converter for comparing said voltage and producing a difference signal;
   means connected to said comparator means and receiving said difference signal for evaluating the size and breakdown characteristics of the particle traversing said measuring passage; and
   a controller responsive to the generation of said difference signal and connected to said function generator for enabling same to apply a constant voltage across said passages for a predetermined period, thereafter to apply a linearly increasing voltage across said passages, and thereafter to restore the constant voltage across said passages.

5. The apparatus defined in claim 4 wherein said controller is responsive to the entry of a particle into said measuring passage to trigger said function generator to apply said constant voltage for a predetermined interval prior to the application of the linearly increasing voltage.

6. The apparatus defined in claim 4, further comprising zero-setting means connected to said comparator means and to said electrodes for superimposing upon voltage applied by said functioning generator, alternating current of frequency of about 1 to 10 kHz and excluding the generation of a difference signal in the absence of the entry of a particle into said measuring passage.

7. The apparatus defined in claim 6 wherein said alternating current has a sinusoidal waveform.

8. The apparatus defined in claim 4 wherein said passages have lengths of about 50 to 500 microns and diameters of about 20 to 200 microns.

9. The apparatus defined in claim 8 wherein said comparator means is a differential amplifier and said converter comprises a pair of operational amplifiers each connected to a respective electrode of said outlet compartments.

10. The apparatus defined in claim 9 wherein an analog-digital converter is connected to the output of said differential amplifier.

* * * * *